United States Patent [19]
Gauthier et al.

[11] Patent Number: 5,348,923
[45] Date of Patent: Sep. 20, 1994

[54] SILICA-BASED SUBSTRATES MODIFIED BY GRAFTING OF POLYALKYLGUANIDINIUM GROUPS, THEIR PROCESS OF MANUFACTURE AND THEIR USE AS CATALYSTS

[75] Inventors: Patricia Gauthier, La Ferte Alais; Philippe Gros, Saint Etienne; Pierre Le Perchec, Lyon; Jean-Pierre Senet, La Chapelle la Reine, all of France

[73] Assignee: Societe Nationale des Poudres et Explosifs - S.N.P.E., Paris, France

[21] Appl. No.: 982,953

[22] Filed: Nov. 30, 1992

[30] Foreign Application Priority Data

Nov. 29, 1991 [FR] France ................................ 91 14847

[51] Int. Cl.$^5$ .............................................. B01J 21/08
[52] U.S. Cl. ........................................ 502/62; 502/60; 502/64; 502/233
[58] Field of Search ...................... 502/10, 60, 62, 64, 502/233; 501/12

[56] References Cited

U.S. PATENT DOCUMENTS

| | | | |
|---|---|---|---|
| 3,597,248 | 8/1971 | Yates | 501/12 |
| 4,613,491 | 9/1986 | Jung et al. | 423/347 |
| 5,026,533 | 6/1991 | Matthes et al. | 423/342 |

FOREIGN PATENT DOCUMENTS

0028107 5/1981 European Pat. Off. .
0168167 1/1986 European Pat. Off. .

*Primary Examiner*—Asok Pal
*Attorney, Agent, or Firm*—Jacobson, Price, Holman & Stern

[57] ABSTRACT

Silica-based substrate surface-modified by grafting covalent links of organic polysubstituted guanidinium groups, and preferably polyakylguanidinium groups. These substrates can be obtained by reacting silica with a polyalkylguanidinium anion, the silanol residual groups of silica being optionally treated with hexamethyldisilazane to stabilize the substrates. These substrates can be used as chlorination and esterification catalysts.

14 Claims, No Drawings

SILICA-BASED SUBSTRATES MODIFIED BY GRAFTING OF POLYALKYLGUANIDINIUM GROUPS, THEIR PROCESS OF MANUFACTURE AND THEIR USE AS CATALYSTS

The present invention refers to silica-based substrates surface modified by grafting of polyalkylguanidinium groups.

Moreover, the invention concerns the production of those substrates and their use as chlorination and esterification catalysts.

The literature proposes various catalysts for chlorination reactions, including the production of carboxylic acid chlorides by reaction of the corresponding acids with a chlorinating agent such as, particularly phosgene, which is most frequently used.

Unfortunately all those catalysts which are at least partially soluble in organic media present two major problems to those skilled in the art.

In order to reach desired purity, it is necessary to eliminate them from the finished product by distillation. That always expensive step is difficult or even impossible to achieve in the case of the thermosensitive acid chlorides or too high molar masses.

For economical reasons, it is often necessary to be able to re-use them without any critical steps, which is always the case when they are recovered in distillation bottoms. These bottoms contain in fact various other often troublesome products.

Moreover, recycling of those catalysts can be impossible due to their decomposition.

Two groups of phosgenation catalysts are mainly described in the literature.

The first group includes the hot phosgenation catalysts which are not fixed to an insoluble substrate.

The prior art [see particularly J. COTTER et al. Chemistry and Industry 8/5/65 pp. 791-3] describes a large quantity of those catalysts which include:
- the tertiary amines and hydrochlorides thereof (Patent FR 2,212,319),
- the N,N-disubstituted amides (U.S. Pat. No. 3,149,155),
- the quaternary ammonium and phosphonium salts (Patent GB 1,159,266), and
- the tetraalkylureas (patent GB 1,161,220).

The catalysts recovered during the distillation steps in the bottoms are generally mixed with a great number of heavy degradation products, which makes their recycling difficult in further phosgenation steps.

It is also noted that various types of those catalysts are thermally unstable, are decomposed into critical by-products and cannot be recovered and re-used.

Further, it has been shown [Patent FR 2,585,351] that hexaalkylguanidinium salts are extremely efficient phosgenation catalysts for carboxylic acids and can be used in very small quantities.

However, although they provide clearly improved results with respect to the other catalysts, it is always necessary to eliminate them by distillation in order to obtain high purity acid chlorides. In addition to the fact that this step is expensive, it is sometimes impossible when the products are too unstable or when their boiling point is too high. People are then obliged to supply an impure product containing waste catalyst and that is not always acceptable for example for pharmaceutical applications.

The second group includes phosgenation catalysts fixed to insoluble substrates.

The above-mentioned problems have not been overlooked by manufacturers of products coming from hot phosgenations. They have thus proposed catalysts chemically fixed to polymers which are insoluble in the organic media, such as polymers of the following structures:

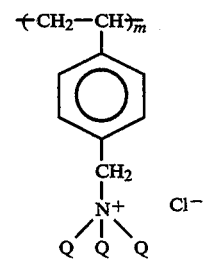

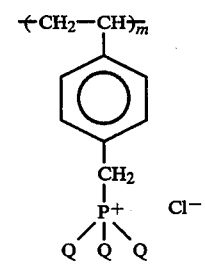

Those polymers derived from chloromethylated polystyrenes are described as phosgenation catalysts of:
- phenols [U.S. Pat. No. 3,211,775]
- mercaptans [Patent FR 2.462.423]
- carboxylic acids [Patent JP 59,108,736; Chemical Abstract 101, 151 439e.

Those are, by example, anion exchange resins crosslinked with 7–8% divinylbenzene, such as the resin sold under the trademark AMBERLITE IRA-400 by ROHM & HAAS.

However, tests made by the applicant have shown that those catalytic systems are inconvenient to use, as they are destroyed during the first use due to the benzyl fragilization being very important as from 80°–90° C., which makes recycling impossible; there is also obtained an impure product.

The benzyl fragilization can be represented schematically by the following way wherein Bu represents the butyl group:

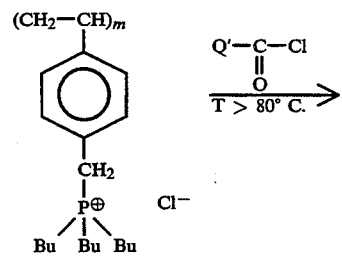

-continued $$+CH_2-CH\rangle_m$$

[benzene ring with $-CH_2Cl$ substituent] + Bu—P+—C—Q'  Cl⁻
with Bu, Bu' on P and =O on C When a chlorinating agent other than phosgene is used so as to obtain acid chlorides, catalysts are also very often necessary. For example, with thionyl chlorides, strong acid chlorides can only be obtained with a catalyst of the same type as those above-mentioned and simultaneously with the same inconveniences.

The production of esters by reaction of carboxylic acids with chloroformates raise numerous problems. Although the use of catalysts, such as 4-dimethylamino pyridine, has been able to improve the yields of that reaction, the selective production of esters is still difficult because of the competing reactions which produce anhydrides and carbonates, particularly when the acids contain sterically cumbersome radicals.

So far as the applicant knows, the prior art does not mention any catalysts fixed to silica-based substrates useful in chlorination reactions of carboxylic acids or esterification reactions through chloroformates.

Organic molecule grafting to such substrates is nevertheless described in the prior art (De Haan et al., J. of Colloid. Inter. Sci., 1986, 110, p. 591), but so far as the applicant knows, grafting of polysubstituted guanidinium groups has never been taught.

The prior art does not describe any efficient stable and easily recyclable catalysts.

The applicant has discovered surprisingly that it was possible to fix polysubstituted guanidinium ions to silica-based substrates.

The applicant has discovered more surprisingly that such substrates make it possible to catalyse chlorination and esterification reactions efficiently and are recyclable by simple methods.

The present invention has thus as an object silica-based substrates surface modified by grafting covalent links of organic groups, characterized in that said groups are polysubstituted guanidinium groups, preferably polyalkylguanidinium groups.

The present invention has more particularly as an object substrates with the following formula (I):

$$R-O-Si(OR)(T)-Y-N(R_1)\cdots[\overset{\oplus}{C}\cdots N(R')-Z-N(R')]_n\cdots\overset{\oplus}{C}-N(R_7)(R_6), (n+1)A^- \quad (I)$$

with N(R_2)(R_3) and N(R_4)(R_5) branches wherein:
R represents the silica-based substrate,
Y represents a $C_2$-$C_{10}$ bivalent alkyl radical, branched or not, having at least 2 carbon atoms on the linear chain between silicon and nitrogen atoms, Y being preferably the radical —$(CH_2)_3$—,
$R_1$, $R_2$, $R_3$, $R_4$, $R_5$, $R_6$, $R_7$, identical or different, represent $C_1$-$C_6$ alkyl radicals, preferably methyl and/or n-butyl radicals,
A represents an anion having only one negative charge, preferably an halogenide ion eventually linked to the corresponding halohydric acid and particularly a chloride ion or an ion $HCl_2^-$,
Z represents a $C_2$-$C_{10}$ bivalent aliphatic radical,
R' represents a $C_1$-$C_4$ alkyl radical,
n=0 or n is an integer generally lower than 10, preferably lower than 5,
T represents:
* a single link with the R substrate
* a group —$Si(R_o)_3$ wherein $R_o$ is a $C_1$-$C_4$ alkyl group, preferably a methyl residue, or
* a $C_1$-$C_4$ alkyl group.

The present invention concerns moreover the trimethoxysilane-polyalkylguanidinium ion of following formula (II):

$$(MeO)_3-SiY-N(R_1)\cdots[\overset{\oplus}{C}\cdots N(R')-Z-N(R')]_n\cdots\overset{\oplus}{C}-N(R_7)(R_6) \quad (II)$$

with N(R_2)(R_3) and N(R_4)(R_5) branches wherein R', Z, Y, n and $R_1$ to $R_7$ have the same meanings as above-mentioned and Me is the methyl radical.

The present invention refers also to a process for production of the above described substrates.

The substrates of formula (I) can be obtained by reaction of the silica-based substrate with a polyalkylguanidinium ion particularly of formula (II).

When n=0, the ion of formula (II) can be itself prepared by reaction of a primary amine with a trimethoxysilylalkyl halogenide, then by reaction of the secondary trimethoxysilylamine obtained with a formamidinium salt. The first reaction is carried out generally with an excess of the amine, possibly in an inert solvent. The second reaction is generally carried out in presence of an organic base such as triethylamine in an inert solvent. The reaction scheme with a chloride anion is as follows:

$$(MeO)_3 SiY-X \xrightarrow{R_1NH_2} (MeO)_3 SiY-NHR_1 \xrightarrow{}$$

$$(MeO)_3SiYN(R_1)\cdots\overset{\oplus}{C}\cdots N(R_7)(R_6) \quad Cl^-$$
with N(R_4)(R_5) branch wherein X is an halogenide, particularly Cl or Br.

When n is different from 0, the ion of formula (II) can be obtained by a first polycondensation step of a diformamidinium salt with a diamine so as to obtain a polyguanidinium having a formamidinium terminal. In a second step, the formerly obtained polyguanidinium is reacted with a trimethoxysilylakylamine so as to obtain a modified polymer and then in a third step this modified polymer is reacted with a formamidinium salt.

The first reaction occurs generally in an inert solvent, such as a chlorinated aliphatic hydrocarbon, for example, dichloroethane or methylene chloride, at a temperature comprised between 20° C. and 100° C. in the presence of an organic base, such as triethylamine. The second and the third steps are carried out in the same conditions.

The reaction scheme with a chloride anion is as follows. If another anion is preferred, it is possible to change anions by treating one of the intermediates with a salt.

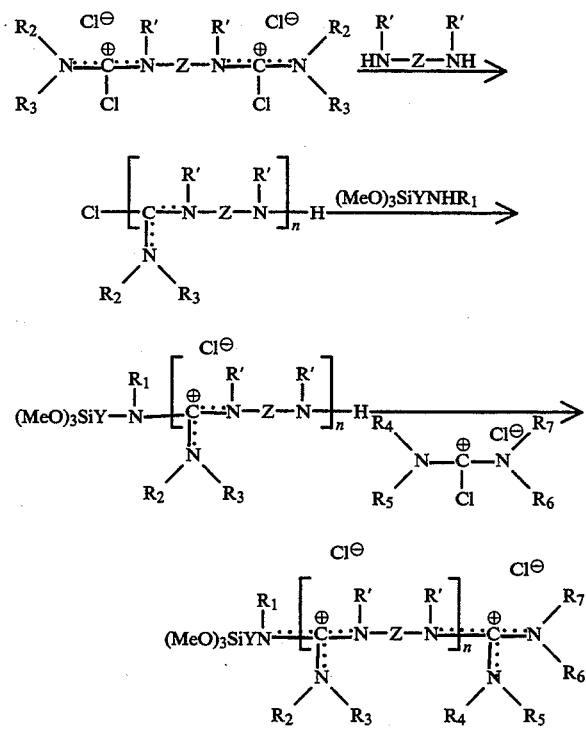

Moreover, it is to be added that the polyalkylchloroammonium chlorides:

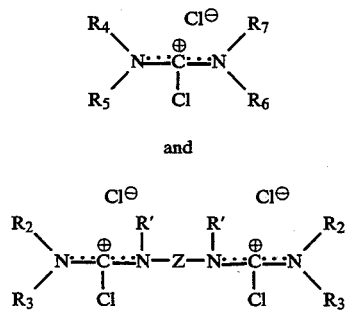

are prepared in a known manner, for example by reaction of phosgene [H. EILINGSFELD Chem. Ber. (1964) 97, p. 1232] or oxalyl chloride [H. ULRICH Angew. Chem. Int. Ed. Engl. (1966) 5 704] with substituted ureas.

The general conditions of functionalization of silicas with —OH surface groups are mentioned in De Haan et al. (J. of Colloid. Inter Sci., 1986, 110, p. 591).

Finally in order to improve the stability of the substrates, the remaining silanol functions of the substrate can be converted by final treatment in a known manner, for example with hexamethyldisilazane, through the following reaction:

The silica-based substrate used is preferably porous under the form of balls the diameter of which is chosen to improve filtrability between 0.01 and 1 mm, preferably between 0.1 and 1 mm. The surface area is comprised between 50 and 750 m$^2$/g, preferably between 50 and 200 m$^2$/g.

The concentration of the surface silanol functions is advantageously about $4.8 \cdot 10^{-6}$ mol/m$^2$.

The formerly described substrates can be used for catalysis of the conversion of carboxylic acids into acid chlorides through chlorinating agents, such as for example phosgene, diphosgene (trichloromethyl chloroformate), triphosgene (hexachlorodimethylcarbonate), thionyl chloride, oxalyl chloride and phosphorus trichloride.

All acids which can be converted into acid chlorides by chlorination with a chlorinating agent can be used as starting materials in the process according to the invention.

For example, said carboxylic acids have the following formula (III):

wherein:
* when m=1
E represents
  a C$_1$–C$_{30}$ linear or branched aliphatic radical, saturated or not, substituted or not,
  a C$_3$–C$_7$ cycloaliphatic radical,
  a substituted or non substituted aromatic radical,
  an heterocyclic radical
* when m is an integer higher than 1
E represents
  a C$_2$–C$_{20}$ linear or branched plurivalent radical, saturated or not, substituted or not,
  a C$_5$–C$_7$ cycloaliphatic radical,
  a substituted or non substituted aromatic radical,
  an heterocyclic radical.

The reaction conditions of chlorination of carboxylic acids through phosgene, diphosgene or triphosgene in presence of catalysts according to the invention are mentioned hereunder.

When working in a discontinuous way, there can be used quantities of compounds of formula [I] corresponding to quantities of fixed guanidinium groups comprised between $10^{-3}$ and $5.10^{-2}$ eq. per eq. of acid function to be converted.

For example, for a silica-based substrate containing 0.2 meq/g grafted guanidinium functions (determination by Cl$^-$ rate), a quantity of catalyst comprised between 5 and 250 g will be used for one mole of monoacid.

When working in a continuous way, the acid and the phosgene or one of its homologues are sent onto a catalyst bed, the flow rate being chosen so that the contact times of the reactants is sufficient.

When it is possible, it is preferred to work without any solvent. In some cases, for example when the acids have high melting points higher than 140° C. or when high quantities of grafted silica are employed, an inert solvent, such as toluene, xylene, chlorobenzene, dichlorobenzenes and others, can be used.

The phosgenation reaction according to the invention is generally carried out at a temperature comprised between 80° C. and 160° C., preferably between 90° C. and 130° C.

The reaction time depends upon the type of acid to be converted, the quantity of guanidinium functions used, the catalyst structure and the temperature. It is generally comprised between 2 and 24 hours approximately.

When another chlorinating agent than phosgene or its derivatives is used, the operating conditions are adjusted dependent on the actual known characteristics of this chlorinating agent. For example with the thionyl chloride, the reactions conditions are the same, but the temperature is generally slightly lower comprised between 50° C. and 100° C.

The chlorination process according to the invention allows to obtain very pure acid chlorides and to recycle totally the used catalysts.

It is known that the carboxylic acid chlorides are synthesis intermediates broadly used in numerous fields of the chemical industry, including pharmaceutics, phytopharmaceutics, polymer chemistry (synthesis of peresters as initiators for radical polymerization for example), manufacture of cosmetics and paper treatment.

The substrates according to the invention can be also used as catalysts to prepare esters by reaction of the carboxylic acids with chloroformates.

All the formerly mentioned acids can be used as starting materials.

The chloroformates known to form esters as, for example, those described in the publication of Kim S., Lee J. I., Kim Y. C. in J. Org. Chem., 1985, 50, 560 can be used. They include particularly the $C_2$–$C_{10}$ aliphatic chloroformates, linear or branched, substituted or not, araliphatic chloroformates substituted or not, aromatic chloroformate substituted or not.

The added quantities of catalysts are generally comprised in the same proportions than above mentioned to obtain the acid chlorides.

The reaction is carried out generally without solvent or with the solvent medium as above mentioned.

The temperature is generally comprises between 80° C. and 140° C., preferably between 110° C. and 130° C.

The catalysts according to the invention are particularly useful to form esters from acids having sterically cumbersome radicals. The esters are obtained selectively with very high yields and a high purity. There are substantially no anhydrides or carbonates simultaneously formed as in the prior processes using other catalysts. The catalysts according to the invention do not lose their properties and are easily recyclable.

The esters are synthesis intermediates which are frequently used for example to protect the acid functions or to couple the aminoacids in peptidic synthesis.

The following examples are presented by way of illustration and not limitation of the present invention:

EXAMPLE 1

Preparation of a Silica-based Substrate of Formula [I] Wherein n=0

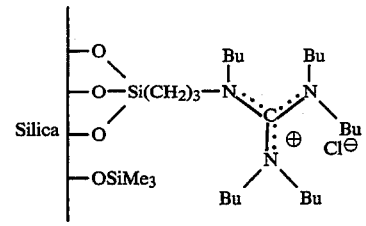

or

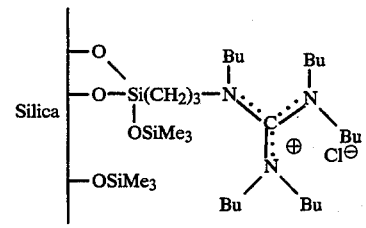

STEP 1

Synthesis of N-butylamino-(Propyl-trimethoxy Silane 22 g (0.3 mol) distilled n-butylamine are heated under reflux (80° C.). 18,6 ml (0,1 mol) (3-chloropropyl)-trimethoxysilane are then added slowly under nitrogen stream. The mixture is maintained under n-butylamine reflux during 12 hours.

After cooling, an abundant precipitate of n-butylamine hydrochloride is obtained the filtration of which is facilitated by addition of 100 ml petroleum ether (45°–60° C.).

The filtrate is then concentrated and the yellow liquid obtained is afterwards purified by distillation at 80° C. under pressure of 13.3 Pa (0.1 mm Hg).

There are obtained 21 g (yield 88%) of a colorless liquid which must be stored secure from light.

Analyses

NMR 80 MHz:delta ppm: 0.6–0.9 (m; 5H; $CH_3$—$CH_2$—; $CH_2$—Si—); 1.2–1.8 (m; 7H; —$CH_2$—; —N—H); 2.5 (q; 4H; —$CH_2$—NH—); −3.4 (s; 9H; $CH_3O$—)

| | Elementary analysis: | | | | |
|---|---|---|---|---|---|
| | % C | % H | % N | % O | % Si |
| Calculated: | 51.02 | 10.71 | 5.95 | 20.39 | 11.93 |
| Found | 50.83 | 10.42 | 5.70 | | *12.25 |

*The oxygen content cannot be measured in presence of silicon.

Step 2

Synthesis of N,N,N′,N′,N″-pentabutyl, N″-propyltrimethoxysilane Guanidinium Chloride To a solution of 10 g (0.042 mol) of the preceding silane and 8.3 ml (0.06 mol) triethylamine in 30 ml dry 1,2-dichloroethane is added slowly under nitrogen stream a solution of 14.2 g (0.042 mol) tetrabutyl-chloro-amidinium (TBCA) chloride in 20 ml 1,2-dichloroethane over 2 hours.

The reaction is slightly exothermic and the precipitation of the triethylamine hydrochloride is immediate.

The reaction medium is stirred at room temperature during 24 hours.

After separation of the hydrochlorides, the filtrate is concentrated and diluted with 20 ml petroleum ether (45°–60° C.). The brown viscous phase obtained is separated and dried in the rotary evaporator during 3 hours at 80° C. under a pressure of 2 kPa (15 mm Hg). In such a way 16 g (71%) of a brown viscous liquid are obtained.

Analysis

IRTF: guanidinium band 1540 cm$^{-1}$
NMR 80 MHz:delta ppm:0.6–1 (m; 17H; $CH_3$—$CH_2$—; $CH_2$—Si—); 1.1–1.9 (m; 22H; —$CH_2$—$CH_2$—); 2.9–3.2 (m; 12H; —$CH_2$—N—C$^+$); 3.6 (s; 9H; $CH_3O$—)

| | Elementary analysis: | | | | | |
|---|---|---|---|---|---|---|
| | % C | % H | % N | % O | % Cl | % Si |
| Calculated: | 60.24 | 11.23 | 7.81 | 8.92 | 6.59 | 5.22 |
| Found | 60.00 | 10.92 | 7.51 | * | 6.79 | 5.35 |

*See analysis of step 1.

Step 3

Grafting of Silane Obtained in Step 2 Onto Silica

To 10 g silica (90 g/m$^2$, 4.8 micromols/m$^2$) in 50 ml dry toluene is added a solution of 3.4 g (6.3.10$^{-3}$ mol) silane from step 2 in 50 ml dry toluene under nitrogen flux.

The mixture is heated under reflux during 24 hours, the solution is then filtrated and silica washed twice with 50 ml dry 1,2-dichloroethane.

Step 4

Blocking of the Remaining Silanol Functions

The formerly obtained silica is treated with a solution of 2.6 ml (0.012 mol) hexamethyldisilazane (HMDS) in 50 ml carbon tetrachloride during 2 hours at room temperature.

The silica is then filtrated and washed during 4 hours in a soxhlet with dichloromethane, and then dried during 12 hours at 60° C. under 2.6 kPa (20 mm Hg).

Analysis

IRTF (diffuse reflection):guanidinium band 1540 cm$^{-1}$ —C—H bands at 2980–2990 cm$^{-1}$

| | Elementary analysis: | | | | |
|---|---|---|---|---|---|
| | % C | % H | % N | % Si | % Cl |
| Found: | 4.37 | 1.14 | 0.65 | 43.40 | 0.60 |
| Chlorine rate: | 0.2 meq./g. | | | | |

EXAMPLE 2

Preparation of a Silica-based Substrate of Formula [I] Wherein n=3, Y=($CH_2$)$_3$—, R'=Me, $R_1=R_2=R_3=R_4=R_5=R_6=R_7$=n—Bu, Z=($CH_2$)$_6$.

Step 1

Synthesis of di N,N,-(dibutylaminocarbonyl) N,N'-dimethyl-hexane-diamine-1,6

To a solution of 4.33 g (0.03 mol) of N,N'-dimethyl-hexane-diamine-1,6 and 10 ml triethylamine (0.07mol) in 100 ml anhydrous benzene is added rapidly under inert atmosphere a solution of 11.5 g (0.06 mol) N,N'-dibutyl carbamoyl chloride in 50 ml anhydrous benzene and the mixture is heated under reflux during 24 hours. After cooling, the mixture is washed four times with 100 ml water, dried on sodium sulfate, dry concentrated and then purified by distillation in a ball oven [P=1.33 Pa (0.01 mm Hg); oven temp.=200° C.].

There is obtained 8.2 g (60%) of a light yellow oil.

IRTF:Urea:band at 1647 cm$^{-1}$; vanishing of the carbamoyl band at 1732 cm$^{-1}$.

NMR $^1$H 80 MHz (CDCl3; TMS) delta ppm: 0.7 (m, 12 H); 1.1–1.7 (m, 24 H); 2.8 (s, 6 H) 3.1 (t, J=7 Hz, 12 H).

Step 2

Synthesis of di (N,N'-dibutyl N-methyl-chloro formamidinium)-1,6 hexane dichloride.

To a solution of 7 g (0.0154 mol) of the diurea obtained in step 1 in 20 ml dry dichloroethane is added a solution of 4 ml (0.046 mol) oxalyl chloride in 10 ml dichloroethane under dry atmosphere, then the mixture is kept reacting during 18 hours at 70° C. (the progression of the reaction is followed by infrared spectrometry and a new quantity of oxalyl chloride (1 ml) is optionally added followed by a new reaction time of 4 hours). When the urea band at 1647 cm$^{-1}$ has completely disappeared, the infrared spectrum (I.R.) shows a single amidinium band at 1625 cm$^{-1}$. The oxalyl chloride in excess is eliminated by degassing with a dry nitrogen stream and the obtained solution is used as such for further condensation with the diamine (step 3).

Step 3

Polycondensation of the Salt of Diformamidinium with the N,N'-dimethylhexane Diamine-1,6

To the former solution is added slowly a solution of 2.8 ml (2.2 g; 0.0153 mol) of diamine in 20 ml dry dichloroethane under dry atmosphere. The temperature is maintained at about 40° C. during the addition. Reaction is then allowed to proceed while stirring during 18 hours at room temperature. The precipitate of triethylamine hydrochloride is then filtrated and the filtrate is concentrated at ½ and extraction is carried out three times with 50 ml bipermuted water. The aqueous phase is dry concentrated, diluted with dichloromethane, dried on sodium sulfate and dry concentrated. Then the resulting phase is washed with hot ethyl acetate, then dissolved in anhydrous acetonitrile and finally dry concentrated under a good vacuum.

There is obtained 8.9 g (yield 90%) of a light brown highly viscous product.

IRTF:Characteristic bands of guanidinium at 1549 and 1567 cm$^{-1}$. Disappearence of the amidinium band at 1 625 cm$^{-1}$.

NMR $^1$H 250 MHz (acetone D$_6$, TMS) delta ppm: 0.95 (t, J=7.1 Hz 6 H); 1.25–1.55 (m, 8 H); 1.55–1.95 (m, 8 H); 3.06–3.27 (m, 6 H); 3.27–3.75 (m; 8 H).

Soluble in acetone, dichloroethane, dichloromethane, acetonitrile and water.

Insoluble in benzene, chloroform and ethyl acetate.

Step 4

Preparation of Silane Polycondensate

To a solution of 7.90 g of the polycondensate of step 3 in 40 ml dry 1,2 dichloroethane is added a solution of 0.7 g (3.10$^{-3}$ mol) N-butylamino-(propyl-trimethoxy silane) and 1.2 ml (8.10$^{-3}$ mol) triethylamine in 5 ml dry 1,2 dichloroethane.

The mixture is heated under reflux during a few hours. After cooling, 1.1 g (3.10$^{-3}$ mol) TBCA in solution in 10 ml dry 1,2 dichloroethane are added. The reaction medium is then hold under stirring at room temperature during 2 hours.

After filtration of the triethylamine hydrochloride, the organic phase is concentrated and washed with 20 ml petroleum ether (45°-60° C.). There is then obtained 8.5 g of a liquid polymer.

Analysis

IRTF: Characteristic bands of guanidinium at 1540 and 1550 cm$^{-1}$.

NMR 80 MHz delta ppm: 0.6 (t, 2 H; $CH_2$—Si—); 0.95 (t, 30 H; $CH_3$—$CH_2$—); 1.5 (m, 70 H; —$CH_2$—$CH_2$—); 3 (s, 18 H; $CH_3N^+$—3.2 (m; 36 H; $CH_2$—N—+); 3.5 (s, 9 H; $CH_3O$—Si).

Step 5

Grafting of Silane Polycondensate to Silica

To 7 g silica (90 m$^2$/g; 4.8 micromoles/m$^2$) in 50 ml dry 1,2 dichloroethane is added a solution of 5.73 g (4.4 mmoles) of the silane-polycondensate from step 4 in 10 ml dry 1,2 dichloroethane. The mixture is heated under reflux during 24 hours.

After cooling, silica is filtrated and washed in the soxhlet during 3 hours with dichloromethane and then dried a few hours at 50° C. under 2.6 kPa (20 mm Hg).

Analysis

IRTF (diffuse reflection): guanidinium band at 1540 cm$^{-1}$

Elementary analysis

Chlorine rate: 0.60% or 0.2 meq/g.

Step 6

Blocking of the Remaining Silanol Functions

Blocking is carried out in the same conditions as those used in example 1, step 4.

Analysis

IRTF (diffuse reflection): guanidinium band at 1540 cm$^{-1}$

Chlorine rate: 0.58%.

EXAMPLE 3

Evaluation of the Catalytic Activity of the Silica-based Substrate of Formula (I) Prepared in Example 1 in Phosgenation of 2-ethyl Hexanoic Acid 1 eq. 2-ethyl hexanoic acid and the quantity corresponding to 0.01 eq. of grafted silica guanidinium are introduced into a reactor. The reaction medium is heated up to 120.5° C. and gaseous phosgene is fed. The progression of the reaction is followed by gas chromatography analysis.

After degassing under argon stream, silica separated by filtration and washed three times with 20 ml (3.5 g silica) chloroform. After washing with dichloromethane in the soxhlet during 2 hours, silica is dried at 80° C. under 2.6 kPa (20 mm Hg) during 18 hours and analysed.

Two other phosgenation steps are carried out in the same way including catalyst treatment from the silica recovered from the former step.

The quantities of materials used and the results obtained are grouped together in the tables I and II hereunder.

It is to be pointed out that no loss of silica weight was observed between the different steps.

EXAMPLE 4

Evaluation of the Catalytic Activity of the Silica-based Substrate of Formula [I] After a Longer Treatment in a Medium of Phosgene and Acid Chloride This example is given to show the very high stability of the catalysts according to the invention.

10 g of the substrate of formula [I] prepared in example 1 are placed into 100 ml 2-ethyl hexanoyl chloride under phosgene sweeping at 120° C. during 64 hours. At the end of that treatment no evolution is observed as concerns the IR spectrum, the chlorine level and the result of the elementary analysis. Chlorine 0.59%; C 3.14%; H 0.82%; N 0.33%.

Phosgenation of 2-ethyl hexanoic acid is repeated in the same conditions as for example 3 with:
3.5 g (0.7 meq.) of the catalyst treated as above-mentioned (120° C.–64 hours)
11.6 g (0.08 mol) 2-ethyl hexanoic acid.

Phosgenation lasts 7 hours and the composition of the product obtained is as follows:
2-ethyl hexanoyl chloride content: 99.9%
2-ethyl hexanoic acid content: 0
Anhydride content: 0.1%.

EXAMPLE 5

Evaluation of the Catalytic Activity of the Ungrafted Silica Used as Starting Material for the Silica-based Substrate of Formula [I] From Example 1

Phosgenation step of example 4 is repeated but with unfunctionalized raw silica (90 m$^2$/g; 4.8 micromoles/m$^2$) with the following quantities:
silica: 3.5 g
2-ethyl hexanoic acid: 11.6 g.

After 8 h phosgenation at 122° C. the operation is stopped. It is noticed that the acid chloride content is only 18%.

EXAMPLE 6

Evaluation of the Catalytic Activity of the Substrate of Formula (I) Prepared in Example 1 for Stearic Acid Phosgenation Everything is made as per example 3, but phosgenation is carried out at 100° C. instead of 120.5° C. with:
10 g (2 meq. Cl$^-$) of the substrate of formula (I) prepared in example 1,
56.9 g (0.2 mol) stearic acid.

The reaction ends after a 6 h phosgenation. The composition of the resulting product is as follows:
stearyl chloride content: 99.7%
stearic acid content: 0
anhydride content: 0.3%

EXAMPLE 7

Continuous Preparation of 2-ethyl Hexanoyl Chloride on a Column of the Substrate of Formula (I) Prepared in Example 1

A column with a double shell heated at 120° C. and filled with the silica-based substrate of formula (I) prepared in example 1 is fed under counterflow:
by 2-ethyl hexanoic acid at the top and by gaseous phosgene at the bottom.

The ratio of the feed rates in mole/hour $COCl_2$/acid is 1.1.

The rates are chosen so that the contact time in the column is 4 hours.

The acid chloride collected at the bottom of the column and degassed (elimination of the phosgene dissolved) has the following composition:

2-ethyl hexanoyl chloride content: 99.7%
2-ethyl hexanoic acid content: 0
anhydride content: 0.3%.

The silica-based substrates modified by grafting polyalkylguanidinium groups according to the invention are valuable phosgenation catalysts for the conversion of carboxylic acids into acid chlorides. They make it possible to obtain excellent yields while being stable and easily recyclable. Due to their favorable properties, they can be used not only in phosgenation reactions with known carboxylic acids already used in that type of reaction, but also to obtain acid chlorides which were difficult to obtain by phosgenation with presently available catalysts.

EXAMPLES 8 TO 10

Preparation of Trichloroacetyl, p-nitrobenzoyl and 3,4,5 trimethoxybenzoyl Chlorides with Diphosgene The general operating way is as follows:

A solution of carboxylic acid (12.2 mmols) in 20 ml chlorobenzene containing 0.7 g (0.122 meq. Cl−) of the catalyst of the same formula as per example 1 (called PBGSiCl hereunder), but prepared from a silica having a slightly lower hydroxyl rate and consequently a chlorine rate of 0.17 meq/g is introduced in a reactor equipped with a methylene chloride/dry-ice refrigerant.

The suspension is heated at 130° C. and 1.5 ml (12.2 millimols) trichloromethyle chloroformate (diphosgene) is added dropwise. The decomposition is instantaneous and a good reflux of phosgene is obtained. When the hydrochloric acid evolution comes to end (4–9 hours) the reaction is stopped. The catalyst is separated by filtration, solvent is evaporated and the remaining residue is purified by distillation.

This particular conditions, the yields and the characteristics of the acid chlorides obtained are grouped together in table 3 below.

EXAMPLES 11 TO 14

Preparation of Trichloroacetyl, Trifluoroacetyl, p-nitro Benzoyl and 3,4,5-trimethoxybenzoyl Chlorides with Thionyl Chloride The general operating way is as follows:

3 ml (40 mmol) of freshly distilled thionyl chloride are added into 17.4 mmols of carboxylic acid and 0.85 g (0.17 meq Cl−) of PBGSiCl catalyst. The reaction mixture is heated at 80° C. and temperature maintained up to the complete vanishing of the characteristic IR band of carboxylic acid (1-8 hours). The reaction is stopped, the catalyst is separated by filtration and the thionyl chloride is evaporated under reduced pressure. Distillation is then carried out so as to obtain the required product.

The particular conditions and the yields obtained for each chloride are grouped together in table 4 below.

EXAMPLES 15 to 23

Preparation of the Esters

The general operating way is as follows:

0.017 mol of chloroformate is added to a stirred suspension of 1 g (0.17 meq Cl−) of PBGSiCl catalyst in 0.017 mol of carboxylic acid, heated at 120° C. The reaction mixture is stirred at the same temperature during 2 to 9 hours until the end of the $CO_2$ and HCl evolution. It is then diluted with anhydrous dichloromethane and the catalyst is eliminated by filtration. Dichloromethane is evaporated and the ester is obtained by distillation.

The results for each example are grouped together in table 5 below.

The characteristics for the esters obtained are as follows:

Phenyl 2-ethyl hexanoate
MP: 50°-51° C.; IRTF(KBr): 1745 cm$^{-1}$; NMR $^1$H (CDCl3; TMS) delta ppm: 2.1-2.2 (s; 9 H); 6.75 (m; 2 H)
Ethyl caprylate BP: 40° C./0.2 mm Hg; IRTF(film): 1740 cm$^{-1}$; NMR $^1$H (CDCl$_3$;TMS) delta ppm: 0.7-2.0 (m; 16 H); 2.3 (t, 1 H); 4.3 ( q, 2 H)
2,2,2-trichloroethyl caprylate
BP: 50 ° C./0.2 mm Hg; IRTF (film): 1760 cm$^{-1}$; NMR $^1$H (CDCl$_3$; TMS) delta ppm: 0.7-2.1 (m; 16 H); 2.5 (t, 2 H); 4.7 (s, 2 H)
Phenyl benzoate
MP: 68°-70° C.; IRTF(film): 1730 cm$^{-1}$; NMR $^1$ H (CDC; TMS) All protons have signals between 6.7 and 7.1 ppm.
2,2,2-trichloroethyl benzoate
BP: 110° C./0.03 mm Hg; IRTF(film): 1740 cm$^{-1}$; MNR $^1$H (CDCl; TMS) delta ppm: 5.0 (s; 2 H) ; 7.5 (m, 3 H); 8.25 (m, 2 H)

Phenyl Mesitoate
MP: 50° C.; IRTF(film) ;1745 cm$^{-1}$; NMR $^1$H (CDCl3; TMS) delta ppm: 2.1-2.2 (s; 9 H); 6.75 (m; 2 H); 7.25 (m, 5 H)
Benzyl mesitoate
MP: 165° C.; IRTF(KBr);1724 cm$^{-1}$; NMR $^1$H (CDCl3; TMS) delta ppm: 2.1-2.2 (s; 9 H); 5.1 (s; 2 H); 6.6 (s, 2 H); 7.2 (m, 5 H)
Phenyl pivalate
BP: 55° C./1 mm Hg; IRTF(film): 1750 cm$^{-1}$; NMR $^1$H (CDCl3; TMS) delta ppm: 1.2 (s; 9 H); 7.2 (m, 5 H);
Benzyl pivalate
BP: 62° C./2 mm Hg; IRTF(film): 1732 cm$^{-1}$; NMR $^1$H (CDCl; TMS) delta ppm: 1.2 (s; 9 H); 5.1 (s, 2 H); 7.2 (m, 5 H)

TABLE 1

| | | | | | | | |
|---|---|---|---|---|---|---|---|
| | Operating conditions for phosgenation reactions | | | | | | |
| | | | | | Composition of resulting acid chloride | | |
| OPERATION N° Op. | Quantity of silica | Quantity of acid | Quantity of COCl2 | Time | Acid chloride content % | Acid content % | Anhydride content % |
| 1 1st phosgenation | 3.5 g (0.7 meq) | 10 g (0.07 mol) | 19.5 g | 7 h | 99 | 0.08 | 0.92 |
| 2 2nd phosgenation (1st recycl.) | 3.4 g | 9.8 g | 18.9 g | 7 h 15 | 99.6 | 0.05 | 0.35 |
| 3 3rd phosgenation | 3.2 g | 9.5 g | 21.6 g | 8 h | 99.3 | 0 | 0.7 |

TABLE 1-continued

Operating conditions for phosgenation reactions

| OPERATION N° Op. | Quantity of silica | Quantity of acid | Quantity of COCl2 | Time | Composition of resulting acid chloride | | |
|---|---|---|---|---|---|---|---|
| | | | | | Acid chloride content % | Acid content % | Anhydride content % |
| (2nd recycl.) | | | | | | | |

TABLE 2

Elementary analysis of silica after each step

| N° ANALYSIS | C % | H % | N % | Cl % |
|---|---|---|---|---|
| 1 1st phosgenation | 3.31 | 0.82 | 0.38 | 0.49 |
| 2 2nd phosgenation | 3.14 | 0.81 | 0.43 | 0.49 |
| 3 3rd phosgenation | 3.20 | 0.78 | 0.39 | 0.57 |

TABLE 3

| Example | Acid | Time (hours) | Yield of acid chloride (a) % | BP or MP °C. | IRTF cm$^{-1}$ | NMR $^1$H (CDCl$_3$) delta ppm |
|---|---|---|---|---|---|---|
| 8 | trichloroacetic | 9 | 92 | BP 115 | film 1805 | |
| 9 | 3,4,5-trimethoxy benzoic | 6 | 90 | BP 90/ 0,1 mm Hg | (KBr) 1754 | 3.9(s, 9H) 7.4(s, 2H) |
| 10 | p-nitro-benzoic | 4 | 85 | MP 72 | (KBr) 1779 | protons 8.2–8.5 |

(a) calculated from isolated compounds.

TABLE 4

| Example | Acid | Time (hours) | Acid chloride: yield % |
|---|---|---|---|
| 11 | trichloroacetic | 5 | 90 (a) |
| 12 | Trifluoroacetic | 7.5 | 70 (b) |
| 13 | 3,4,5-trimethoxy benzoic | 2 | 90 (a) |
| 14 | p-nitrobenzoic | 1 | 94 (a) |

(a): calculated from isolated compounds.
(b) the gazeous trifluoroacetyl chloride has been trapped by the N,N-dibutylamine and has been characterized and its yield calculated under the form of N,N-dibutyl trifluoroacetamide. BP 60° C./0.05 mm Hg; IRTF 1691 cm$^{-1}$; NMR $^1$H (CDCl$_3$, delta ppm): 0.9(t, 6 H); 1–1.6(m, 8 H); 3.35(t, 4 H)

TABLE 5

| Ex. | Acids (RCOOH) R | Chloroformates (R'OCOCl) R' | Time (hours) | T °C. | Yield (a) % RCOOR' (others) | Yield (b) Lit. |
|---|---|---|---|---|---|---|
| 15 | CH3(CH2)3CH<br>\|<br>C2H5 | C6H5 | 9 | 120 | 98 (<1) | — |
| 16 | CH3(CH2)6 | C2H5 | 4 | 120 | 95 (<1) | — |
| 17 | CH3(CH2)6 | CH2CCl3 | 2 | 120 | 83 (<1) | 90 (10) (c) |
| 18 | C6H5 | C6H5 | 5 | 120 | 92 (<1) | — |
| 19 | C6H5 | CH2CCl3 | 3 | 120 | 84 (<1) | 20 (80) (c) |
| 20 | 2,4,6 (CH3)3C6H2 | C6H5 | 8 | 120 | 97 (<1) | — |
| 21 | 2,4,6 (CH3)3C6H2 | CH2C6H5 | 8 | 120 | 96 (<1) | 0 (98) (d) |
| 22 | (CH3)3C | C6H5 | 9 | 120 | 83 (<1) | — |
| 23 | (CH3)3C | CH2C6H5 | 8 | 120 | 95 (<1) | 47 (52) (e) |

(a): Yield calculated from isolated products for the esters; for the other products Between brackets, the yield is determined by NMR $^1$H
(b): According to the publication of Kim S. et al, J. Org. Chem. 1985, 50, 560 with 10 to 50% 4-(dimethylamino) pyridine in CH$_2$Cl$_2$, 0–25° C., 0.3–1 hour, in presence of a stoichiometric quantity of triethylamine
(c): Ratio ester/carbonate
(d): 98% anhydride
(e): 52% anhydride

We claim:

1. A silica-based substrate having a surface which is modified by grafted covalent links of organic groups, wherein each such organic group is a guantidinium group, each nitrogen atom of which is substituted.

2. A substrate according to claim 1 characterized in that it has the following formula (I):

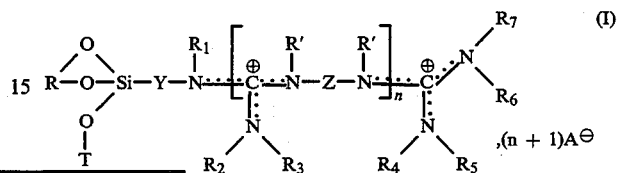

wherein:
R represents the silica-based substrate,
Y represents a $C_2$-$C_{10}$ bivalent alkyl radical, branched or not, having at least 2 carbon atoms on the linear chain between silicon and nitrogen atoms,
Z represents a $C_2$-$C_{10}$ bivalent aliphatic radical,
R' represents a $C_1$-$C_4$ alkyl radical,
$R_1$, $R_2$, $R_3$, $R_4$, $R_5$, $R^6$, $R_7$, identical or different, represent $C_1$-$C_6$ alkyl radicals,
A represents an anion having only one negative charge and,
n=0 or n is an integer,
T represents:
* a single link with the R substrate

* a group —Si($R_o$)$_3$ wherein $R_o$ is a $C_1$–$C_4$ alkyl group, preferably a methyl radical, or
* a $C_1$–$C_4$ alkyl group.

3. A substrate according to claim 2 characterized in that Y represents a —(CH$_2$)$_3$— radical.

4. A substrate according to claim 2 wherein each of $R_1$ to $R_7$ represents a methyl and/or n-butyl radical.

5. A substrate according to claim 2 wherein A represents a halogenide ion.

6. A substrate according to claim 1 comprising silanol functions in the form of ROSi (CH$_3$)$_3$, wherein R represents the silica-based substrate.

7. A trimethoxylsilane polyalkylguanidinium ion of the formula (II):

$$(MeO)_3SiYN\begin{matrix}R_1\\|\end{matrix}\cdots\overset{\oplus}{C}\cdots N-Z-N\cdots\overset{\oplus}{C}\cdots N\diagup^{R_7}_{R_6} \quad (II)$$

wherein
Y represents a $C_2$–$C_{10}$ bivalent alkyl radical, branched or not, having at least two carbon atoms in a linear chain between silicon and nitrogen atoms;
Z represents a $C_2$–$C_{10}$ bivalent aliphatic radical;
R' represents a $C_1$–$C_4$ alkyl radical;
each of $R_1$, $R_2$, $R_3$, $R_4$, $R_5$, $R_6$, and $R_7$ is, independently, a $C_1$–$C_6$ alkyl radical;
n is 0 or an integer; and
Me is methyl.

8. A process for preparing substrates according to claim 1 by reacting of silica with a polyalkylguanidinium ion.

9. A process according to claim 8 wherein the polyalkylguanidinium ion is an ion of formula (II):

$$(MeO)^3SiYN\cdots\overset{\oplus}{C}\cdots N-Z-N\cdots\overset{\oplus}{C}\cdots N\diagup^{R_7}_{R_6} \quad (II)$$

wherein n is 0 or an integer,
Y represents a $C_2$–$C_{10}$ bivalent alkyl radical, branched or not, having at least 2 carbon atoms on the linear chain between silicon and nitrogen atoms,
Z represents a $C_2$–$C_{10}$ bivalent aliphatic radical,
R' represents a $C_1$–$C_4$ alkyl radical,
$R_1$ to $R_7$ are identical or different and represent $C_1$–$C_6$ alkyl radicals, and
Me represents the methyl radical.

10. A process according to claim 9 characterized in that when n=0 the polyalkylguanidinium ion is obtained by reaction of a primary amine with a trimethoxysilylalkyl halogenide, and then by reaction of the resulting secondary trimethyoxysilylamine with a formamidinium salt.

11. A process according to claim 9 characterized in that when n is different from 0 the polyalkylguanidinium ion is obtained by polycondensation of a diformamidinium salt with a diamine and then by reaction of the resulting polyguanidinium with a trimethoxysilylalkylamine and finally by reaction of the resulting polymer with a formamidinium salt.

12. A process according to claim 8 characterized in that the resulting substrate is then treated with hexamethyldisilazane.

13. A silica-based substrate according to claim 1 wherein each substituted guanidinium group is a polyalkylguanidinium group.

14. A substrate according to claim 2 wherein A represents a chloride ion or an HCl$_2$ ion.

* * * * *